United States Patent
Lyden et al.

(10) Patent No.: US 10,591,429 B2
(45) Date of Patent: Mar. 17, 2020

(54) CONTROL CIRCUIT FOR USE WITH A FOUR TERMINAL SENSOR, AND MEASUREMENT SYSTEM INCLUDING SUCH A CONTROL CIRCUIT

(71) Applicant: Analog Devices Inc., Norwood, MA (US)

(72) Inventors: Colin G. Lyden, Baltimore (IE); Donal Bourke, Mallow (IE); Dennis A. Dempsey, Newport (IE); Dermot G. O'Keeffe, County Cork (IE); Patrick C. Kirby, Limerick (IE)

(73) Assignee: Analog Devices, Inc., Norwood, MA (US)

( * ) Notice: Subject to any disclaimer, the term of this patent is extended or adjusted under 35 U.S.C. 154(b) by 451 days.

(21) Appl. No.: 15/187,398

(22) Filed: Jun. 20, 2016

(65) Prior Publication Data
US 2017/0023506 A1    Jan. 26, 2017

Related U.S. Application Data

(60) Continuation of application No. 14/158,416, filed on Jan. 17, 2014, now abandoned, which is a division of
(Continued)

(51) Int. Cl.
*G01N 27/327* (2006.01)
*G01N 27/02* (2006.01)
(Continued)

(52) U.S. Cl.
CPC ....... *G01N 27/028* (2013.01); *G01N 27/3273* (2013.01); *G01N 27/49* (2013.01);
(Continued)

(58) Field of Classification Search
CPC .. G01N 27/028; G01N 27/49; G01N 27/3273; H03F 3/45475; H03F 1/34; H03F 2200/261; H03F 2200/462; H03L 5/00
See application file for complete search history.

(56) References Cited

U.S. PATENT DOCUMENTS

| 5,889,393 | A | 3/1999 | Wrathall |
| 6,011,431 | A | 1/2000 | Gilbert |

(Continued)

FOREIGN PATENT DOCUMENTS

| CN | 1307398 A | 8/2001 |
| CN | 1677299 A | 10/2005 |

(Continued)

OTHER PUBLICATIONS

"U.S. Appl. No. 14/158,416, Appeal Brief filed Dec. 21, 2015", 9 pgs.

(Continued)

*Primary Examiner* — J. Christopher Ball
(74) *Attorney, Agent, or Firm* — Schwegman Lundberg & Woessner, P.A.

(57) ABSTRACT

A control circuit for use with a four terminal sensor, the sensor having first and second drive terminals and first and second measurement terminals, the control circuit arranged to drive at least one of the first and second drive terminals with an excitation signal, to sense a voltage difference between the first and second measurement terminals, and control the excitation signal such that the voltage difference between the first and second measurement terminals is within a target range of voltages, and wherein the control circuit includes N poles in its transfer characteristic and N−1 zeros in its transfer characteristic such that when a loop gain (Continued)

falls to unity the phase shift around a closed loop is not substantially $2\pi$ radians or a multiple thereof, where N is greater than 1.

24 Claims, 11 Drawing Sheets

Related U.S. Application Data application No. 13/626,630, filed on Sep. 25, 2012, now Pat. No. 8,659,349.

(51) Int. Cl.
　　*H03L 5/00* 　　(2006.01)
　　*G01N 27/49* 　　(2006.01)
　　*H03F 1/34* 　　(2006.01)
　　*H03F 3/45* 　　(2006.01)

(52) U.S. Cl.
　　CPC ........... *H03F 1/34* (2013.01); *H03F 3/45475* (2013.01); *H03L 5/00* (2013.01); *H03F 2200/261* (2013.01); *H03F 2200/462* (2013.01)

(56) References Cited

U.S. PATENT DOCUMENTS

| | | | |
|---|---|---|---|
| 7,023,263 | B2 | 4/2006 | Chang et al. |
| 7,659,753 | B2 | 2/2010 | Chen et al. |
| 7,919,959 | B2 | 4/2011 | Chung et al. |
| 8,659,349 | B1 | 2/2014 | Lyden et al. |
| 2004/0021518 | A1 | 2/2004 | Wrathall |
| 2005/0184711 | A1 | 8/2005 | Chen et al. |
| 2010/0066378 | A1 | 3/2010 | Ahmadi et al. |
| 2013/0194034 | A1 | 8/2013 | Giuroiu |
| 2014/0132325 | A1 | 5/2014 | Lyden et al. |

FOREIGN PATENT DOCUMENTS

| | | | |
|---|---|---|---|
| CN | 1818819 | A | 8/2006 |
| EP | 1387478 | A2 | 2/2004 |
| TW | 588393 | B | 5/2004 |

OTHER PUBLICATIONS

"U.S. Appl. No. 14/158,416, Appeal Decision mailed Oct. 20, 2015", 2 pgs.
"U.S. Appl. No. 14/158,416, Decision on Pre-Appeal Brief Request mailed Aug. 200, 2015", 6 pgs.
"U.S. Appl. No. 14/158,416, Examiner's Answer mailed Apr. 21, 2016", 10 pgs.
"U.S. Appl. No. 14/158,416, Final Office Action dated Apr. 20, 2015", 10 pgs.
"U.S. Appl. No. 14/158,416, Non Final Office Action dated Oct. 30, 2014", 8 pgs.
"U.S. Appl. No. 14/158,416, Response filed Mar. 27, 2015 to Non Final Office Action dated Oct. 30, 2014", 4 pgs.
"Chinese Application Serial No. 201310445679, Office Action dated Feb. 15, 2016".
"European Application Serial No. 13185048.9, Extended European Search Report dated Mar. 6, 2014", 8 pgs.
"Taiwanese Application Serial No. 102134360, Office Action dated Jan. 12, 2015", with EN translation, 13 pgs.
Ahmadi, M M, et al., "Current-Mirror-Based Potentiostats for Three-Electrode Amperometric Electrochemical Sensors", IEEE Transactions on Circuits and Systems, I: Regular Papers, IEEE, US, (Jul. 1, 2009), 1339-1348 pgs.
Wen-Yaw, Chung, et al., "A 600μW Readout Circuit with Potentiostat for Amperometric Chemical Sensors and Glucose Meter Applications", 2007 IEEE Conference on Electron Devices and Solid-State Circuits, (Dec. 20, 2007), 1087-1090.
"U.S. Appl. No. 13/626,630, Notice of Allowance dated Oct. 10, 2013", 11 pgs.
"U.S. Appl. No. 13/626,630, Response filed Sep. 20, 2013 to Restriction Requirement dated Aug. 20, 2013", 7 pgs.
"U.S. Appl. No. 13/626,630, Restriction Requirement dated Aug. 20, 2013", 7 pgs.
"Chinese Application Serial No. 201310445679, Office Action dated Jun. 10, 2015".
"Chinese Application Serial No. 201310445679, Office Action dated Aug. 1, 2016", 3 pgs.
"Chinese Application Serial No. 201310445679, Response filed Apr. 27, 2016 to Office Action dated Feb. 15, 2016".
"Chinese Application Serial No. 201310445679, Response filed Oct. 2, 2015 to Office Action dated Jun. 10, 2015".
"Chinese Application Serial No. 201310445679, Response filed Oct. 17, 2016 to Office Action dated Aug. 1, 2016", With English Translation of Claims, 9 pgs.
"European Application Serial No. 13185048.9, Noting of loss of rights dated Jun. 26, 2014", 2 pgs.
"European Application Serial No. 13185048.9, Response filed Oct. 3, 2014 to Extended European Search Report dated Mar. 6, 2014", 15 pgs.

CONTROL CIRCUIT FOR USE WITH A FOUR TERMINAL SENSOR, AND MEASUREMENT SYSTEM INCLUDING SUCH A CONTROL CIRCUIT

CROSS-REFERENCE TO RELATED APPLICATIONS

This is a Divisional Application of U.S. Utility application Ser. No. 13/626,630, filed Sep. 25, 2012, which is incorporated herein in its entirety.

FIELD OF THE INVENTION

The present invention relates to a control circuit for use with a four terminal sensor, a combination of a four terminal sensor and a control circuit, and a method of improving accuracy of a measurement system when used with four terminal sensor. The sensor may, for example be a biological sensor such as a glucose sensor.

SUMMARY OF THE INVENTION

According to a first aspect of the present invention there is provided a control circuit for use with a four terminal sensor, the sensor having first and second drive terminals and first and second measurement terminals, the control circuit arranged to drive at least one of the first and second drive terminals with an excitation signal, to sense a voltage difference between the first and second measurement terminals, and to control the excitation signal such that the voltage difference between the first and second measurement terminals is within a target range of voltages, and wherein control circuit includes N poles in its gain-frequency transfer characteristic and N−1 zeros in its gain-frequency transfer characteristic such that when a loop gain falls to unity the phase shift around a closed loop is not substantially $2\pi$ radians or a multiple thereof, where N≥2 and is an integer.

It is thus possible to perform impedance measurements of the impedance of the four terminal sensor at a plurality of frequencies using a higher gain in the control circuit than would have been the case if stability had been achieved merely by reducing the open loop gain at low frequency until such time as the closed loop gain in the control circuit had fallen to unity whilst maintaining the change in gain with frequency at substantially −20 dB per decade change in frequency.

The N poles and N−1 zeroes referred to above are poles and zeroes occurring at frequencies where the control circuit has sufficient gain for oscillation to occur. This means, for example, that the gain in a forward path within the loop is greater than unity. Preferably a gain margin is included in the loop to allow for manufacturing variation or temperature variation, and hence the N poles and N−1 zeroes referred to in the summary of the invention occur at frequencies where the gain is more than unity as modified by the gain margin, so say at gains of 0.5, or less, such as 0.3.

Poles occurring in the frequency space above the frequency at which the controller gain or loop gain has fallen to less than unity, preferably as modified by a gain margin, such that the gain is, for example, less than 0.5 do not give rise to instability and can be ignored.

The use of higher gains in the control circuit means that the voltage difference between the first and second measurement terminals can be more tightly controlled to a target value or target range of values and consequently measurements of other parameters will also be correspondingly improved.

Advantageously the control circuit has first and second reference voltage input terminals for accepting a differential reference voltage. The differential reference voltage sets the target voltage for the voltage difference between the first and second measurement terminals.

Advantageously the four terminal sensor comprises a load whose impedance varies, amongst other things, as a function of concentration of a chemical, enzyme, or biological material. Alternatively the impedance of a load may vary as a function of a reaction. It is known that sensors for electrical detection of biological parameters can be produced. Examples of such electrically readable biological sensors in widespread use include blood glucose measurement strips that are used in the care of diabetes.

According to a second aspect of the present invention there is provided a control circuit constituting an embodiment of the first aspect of the invention in combination with a four terminal sensor.

According to a third aspect of the invention there is provided a method of operating an instrument loop comprising a multi terminal sensor and an excitation circuit, wherein the multi-terminal sensor has at least one drive terminal which is distinct from a first sense terminal, and wherein the multi-terminal sensor has further terminal, and wherein the excitation circuit is arranged to measure a voltage difference between the first sense terminal and the further terminal, and to use this voltage difference to control an excitation signal applied to the at least one drive terminal so as to maintain the voltage difference between the first sense terminal and the further terminal to a target value or to within a target range, and wherein the excitation circuit is arranged to have at least one zero in its transfer characteristic such that it satisfies the Barkhausen stability criterion.

Preferably the at least one zero is positioned below a frequency at which a forward gain of the excitation circuit has fallen to less than unity such that a closed loop involving the excitation circuit cannot undergo self sustaining oscillation.

DESCRIPTION OF THE FIGURES

The present invention will now be described, by way of non-limiting example, with reference to the accompanying Figures, in which.

DESCRIPTION OF EXAMPLE EMBODIMENTS

Figure 1:
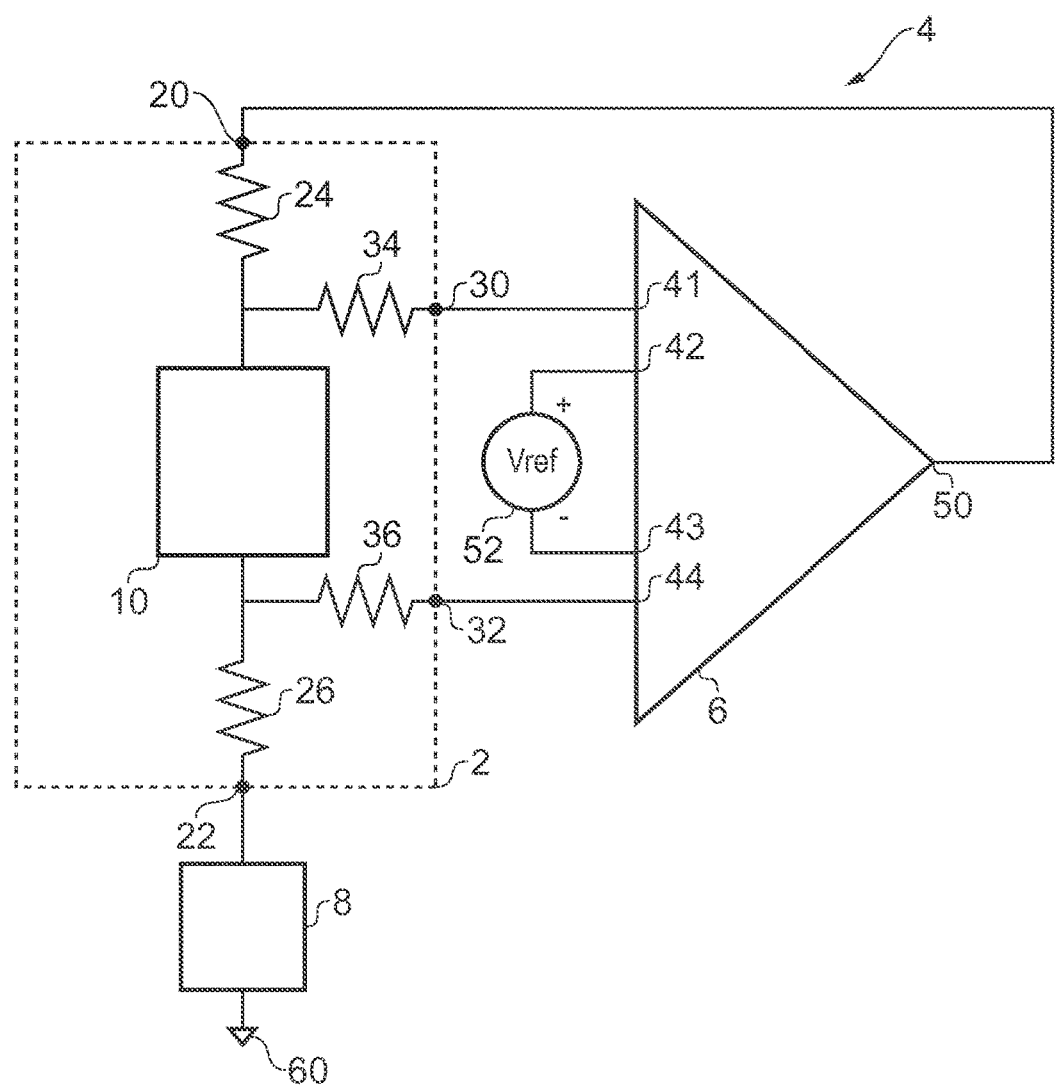
FIG. 1 is a circuit diagram of a measurement circuit constituting an embodiment of the present invention.

FIG. 1 is a circuit diagram of a measurement circuit comprised of a four terminal sensor, generally designated 2, in combination with a control circuit, designated 4, and a current measurement circuit designated 8. The four terminal sensor comprises a load 10 whose impedance varies as a function of a measurand. Thus, for example, the load may be a cell for biological measurement whose impedance varies as a function of an analyte concentration. The analyte may, for example be blood glucose. The cell may be attached to a substrate and connected to terminals on the substrate such that the cell 10 can be electrically excited and the current flow through the cell monitored. As part of this measurement it may be desired to know, with significant accuracy, the voltage across the cell 10 as well as the current through it. Connections to and from the cell 10 may be subject to manufacturing variation and may exhibit impedance, and indeed changes in impedance, which would effect the accuracy of the voltage measurement. In order to overcome such impedance issues, the cell is provided as part of a four terminal sensor. The four terminal sensor comprises a first drive terminal 20, notionally connected to one end of the cell, and a second drive terminal 22 notionally connected to an opposing end of the cell. An impedance, represented by resistor 24 may exist between the first drive terminal 20 and the first end of the cell 10. This first impedance 24 may be deliberate or it may simply be a function of the properties of the cell 10 and the connections made to it and hence may be regarded as being a parasitic component. Similarly a second resistance 26 may exist in the path between the second side of the cell 10 and the second drive terminal 22. The four terminal sensor overcomes the problem of these resistances 24 and 26 by having first and second measurement terminals 30 and 32 connected to the first and second ends of the cell 10, respectively. These connections may also exhibit deliberate or parasitic impedance as represented by resistors 34 and 36, respectively. Although the word "terminal" has been used here, it is to be understood that it can be replaced by the term "node".

The cell output voltages occurring at the first and second measurement terminals 30 and 32 will accurately represent the voltage difference across the cell 10 if no current, or substantially no current, is taken by a measurement circuit connected to those first and second measurement terminals 30 and 32. This condition can, to all intents and purposes be achieved by operational amplifiers employing high impedance front ends. Such high impedance front ends typically use insulated gate field effect transistors as input devices. As a consequence such circuits draw substantially no current from the measurement terminals.

The control circuit 6 has been schematically represented as an operational amplifier. This is substantially correct, because although it has first to fourth inputs 41 to 44 its action within the closed loop shown in FIG. 1 is to drive the voltage at its output node 50 so as to minimize the sum of the voltage difference between the voltage occurring at input 41 with respect to the voltage occurring at input 42 and the voltage difference between the signal occurring at signal input 44 with respect to the signal occurring at reference voltage input 43. Each of these differences can be formed by operational amplifiers i.e. the difference between the signals at inputs 41 and 42, and the difference between the signals at inputs 43 and 44, and then each of these differences can act as inputs to a further operational amplifier.

It will be appreciated that a small voltage difference exists between the value of the first input 41 and the second input 42, and also between the voltage at the input 43 and the input 44, but that the magnitude of this voltage difference depends upon the gain of the control circuit 6. In broad terms, the magnitude of the voltage difference decreases proportionately with the increase in gain of the control circuit 6. Thus high gains within the control circuit 6 result in the voltage difference across the cell 10 being controlled such that it accurately matches the voltage difference generated by a reference circuit 52 and supplied to reference inputs 42 and 43 of the control circuit 6. The effect of the input offsets have been ignored, and it is assumed that appropriate techniques, such as auto-zeroing, will be employed to reduce these sources of error.

In order for the voltage across the cell 10 to be controlled, current must flow through the cell, for example from the first drive terminal 20 to the second drive terminal 22. As part of the measurement of the biological material to which the cell is responsive, it is necessary to know the magnitude of the current passing through the cell. To this end, a current measurement circuit 8 is provided. In the example shown in FIG. 1 the measurement circuit 8 has been positioned between the second drive terminal 22 and a small signal ground 60. However the current measurement circuit 8 could also be provided in the feedback loop between the output node 50 of the control circuit 6 and the first driven node 20 of the four terminal sensor 2. The person skilled in the art is free to make this choice depending, to some extent, on what current measuring technology or circuit he finds most convenient to implement.

The voltage reference 52 may be arranged to generate a DC voltage pulse, in which case it is desirable to measure the evolution of current with respect to time. However, for checking and calibration purposes it may also be desirable for the voltage reference 52 to generate a changing signal, for example an alternating sinusoid, and in which case it becomes desirable for the measurement circuit 8 to have knowledge of the phase of the sinusoidal signal such that a magnitude and phase change of the current flow may be measured, for example to deduce a complex impedance of the cell 10. The complex impedance may be determined by comparing the magnitude and phase of the voltage difference between the first and second measurement terminals with the magnitude and phase of current flow through the sensor.

Figure 2:
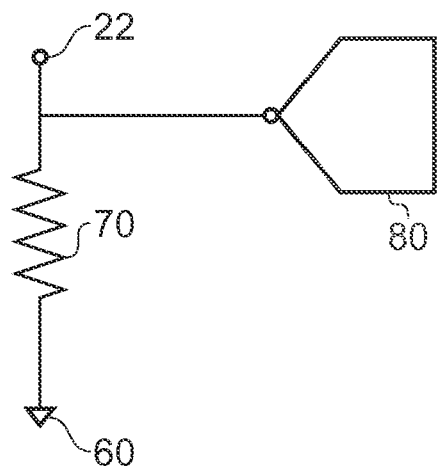
FIG. 2 is a circuit diagram of a current measurement circuit.

FIG. 2 schematically illustrates a first current measurement circuit which comprises a sense resistor 70 disposed in series between the second driven node 22 and the small signal ground 60. The voltage occurring across the resistor 70 can be measured by a analog to digital converter 80. The analog to digital converter 80 may be implemented in any suitable converter technology, such as sigma-delta, successive approximation or flash technologies depending on the speed and accuracy requirements required by the circuits designer.

Figure 3:
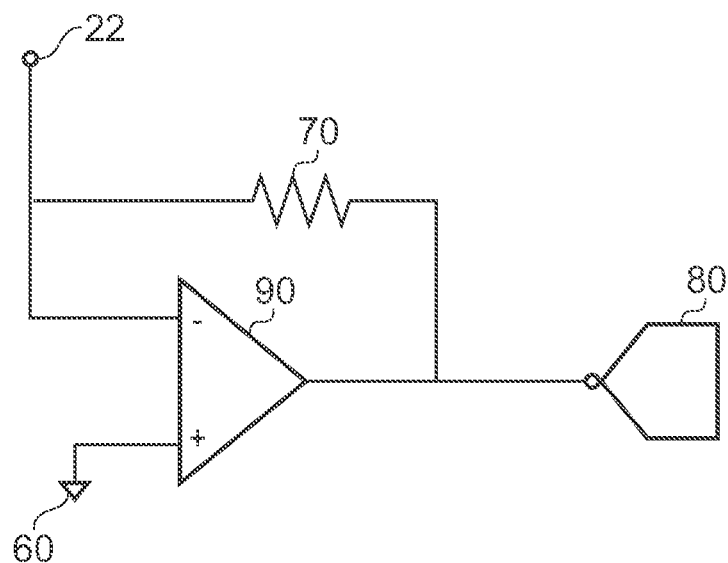
FIG. 3 is a circuit diagram of a further current measurement circuit.

FIG. 3 shows a variation on FIG. 2 in which the current sense resistor is placed in the feedback loop of a operational amplifier 90 having its inverting input connected to the second drive terminal 22 and its non-inverting input connected to the small signal ground 60. This configuration may be advantageous as it means that the voltage at the second drive terminal 22 is held substantially constant by virtue of the amplifier 90 forming a virtual earth, and the impedance of the resistor 70 may be selected so as to give a greater output voltage range at the output of the amplifier 90. Once again, the output voltage can be digitized by an analog to digital converter 80.

Figure 4:
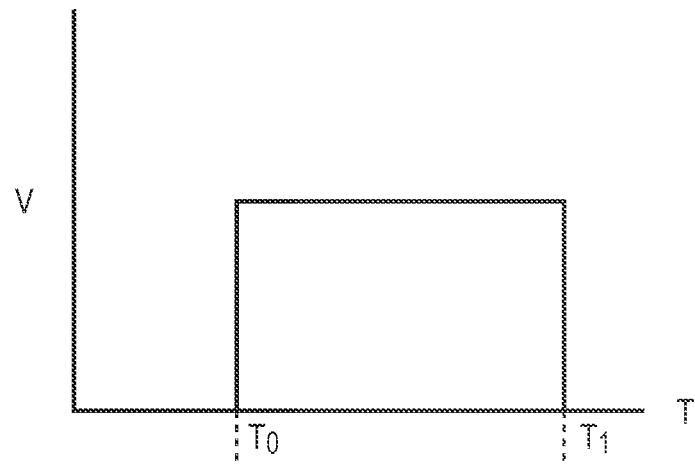
FIG. 4 is a graph representing an excitation signal that may be applied in electrochemical analysis to a suitable measurement cell.
Figure 5:
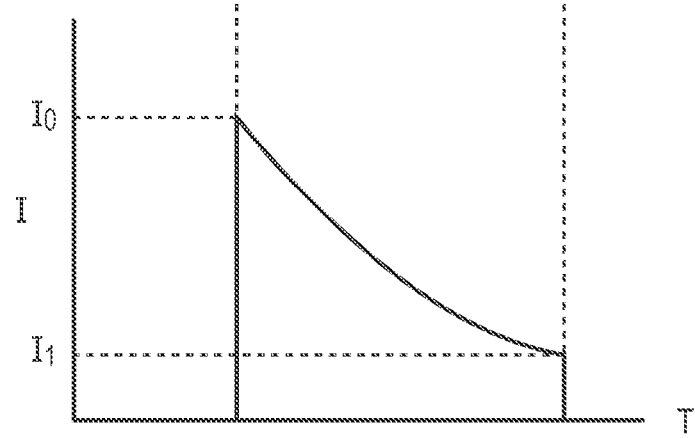
FIG. 5 is a graph of the idealized evolution of current with respect to time for an electrochemical glucose measurement cell.

The load 10 may, for example, be an electronically measured electrochemical strip, of which a glucose strip is a common example. An amperometric measurement protocol for such a strip is illustrated in FIG. 4. During the amperometric measurement, a DC voltage is applied across the strip at time $T_0$ and held constant until time $T_1$. The difference between time $T_1$ and $T_0$ is substantially 1 second and the magnitude of the voltage may be around 500 mV. During the measurement protocol the current across the cell varies substantially as shown in FIG. 5. Thus the current quickly rises to an initial value $I_0$ and decays to a value $I_1$. The curved shape is a cottrellian curve (it follows a Cottrell equation) whose shape varies substantially as $$\frac{K}{\sqrt{T}}.$$

The value of the parameter K varies as a function of analyte concentration. However, the value of K may also vary as a function of other parameters, a common one being temperature, but it may also vary in the presence of contaminants. In a more complex form of the Cottrell equation, the value of K varies as the square root of a diffusion coefficient for a species being measured, and it is the diffusion coefficient which is a function of temperature. It is therefore desirable to make some correction measurements, either before or after the main test, to deduce factors which may be used to modify the value of K, such that, for example, a glucose test becomes more accurate.

Figure 6:
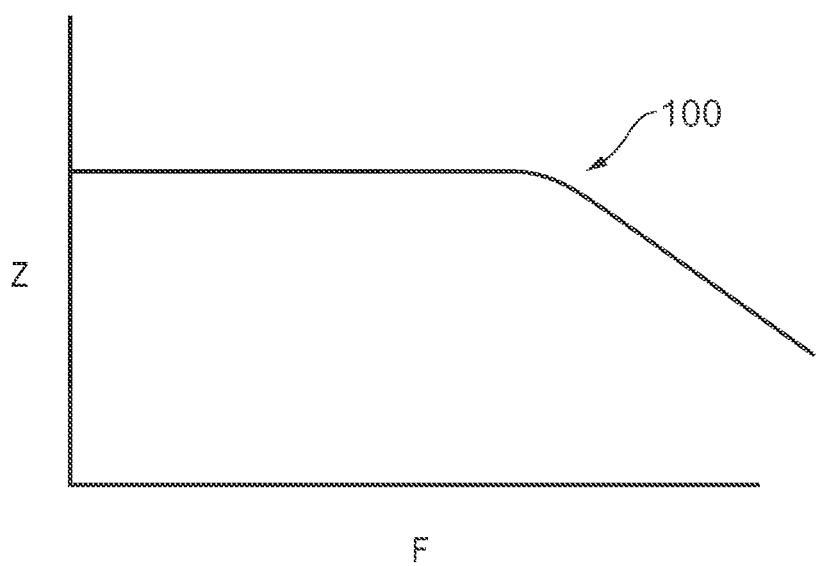
FIG. 6 is a graph of impedance versus frequency for a blood glucose test sensor.

It has been observed by workers in the field that some of these error sources, such as temperature and sonic interfering chemicals can be deduced by measuring the complex impedance of the cell 10. Thus, for example, it has been observed for a glucose measurement cell that the variation of impedance with respect to frequency as shown in FIG. 6, has a turning point generally indicated 100. The position of the turning point can, as known to the person skilled in the art, be used to derive a correction factor, for example, for measurement of temperature. Thus measuring the impedance as a function of frequency enables the temperature of the cell 10 to be deduced. It is expected that this approach can be extended to many biological sensors responsive to respective analytes.

If, for example, one wished to measure the temperature, it might be thought that temperature measurement would be better performed by fabricating a temperature sensor within the cell, but this is not as desirable as might first be supposed. Firstly, a temperature sensor would almost certainly tend to measure the temperature of the substrate upon which the cell is formed rather than a temperature of the cell. Thus, when a biological sample, such as blood, is introduced into the measurement cell the cell's temperature will differ from that of the substrate and an equalization time would be required during which a reaction may occur between chemicals (analytes) in the sample, such as glucose, and the agents within the cell used to test for those chemicals. Additionally the formation of a temperature sensor would require additional processing steps and the temperature sensor itself would probably be subject to manufacturing error and hence may not actually improve the temperature measurement, and hence estimates of related parameters such as diffusivity.

Typically the complex impedance of the cell is measured by inducing a low voltage sine wave across the cell, for example of the order of 15 mV, at a range of frequencies such as 1 kHz, 2 kHz, 10 kHz and 20 kHz. This impedance can be used, in a known way, to apply a correction factor for temperature. This, however, brings its own measurement problems.

Figure 7:
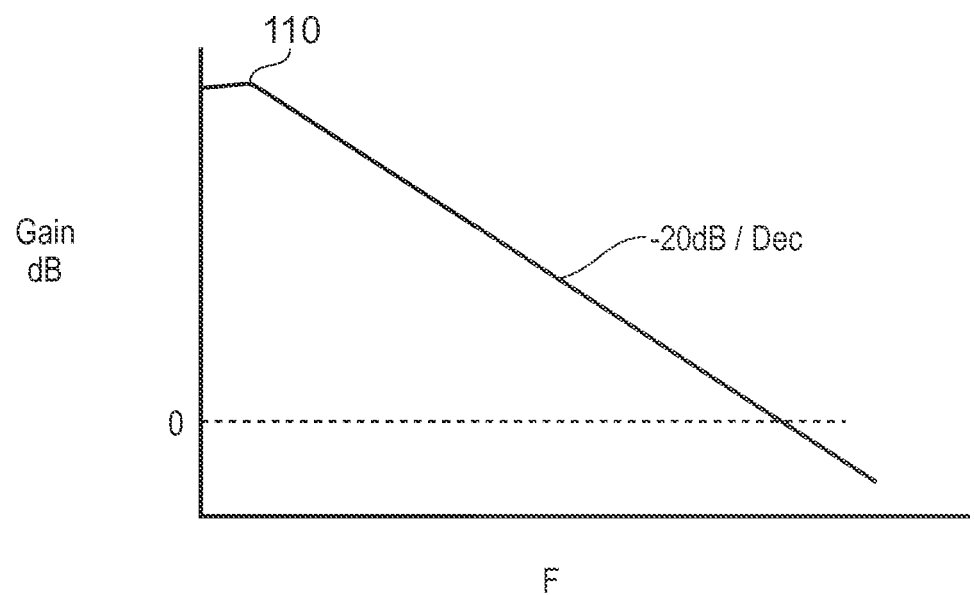
FIG. 7 is a gain-frequency transfer characteristic of an operational amplifier that has been stabilized by its manufacturer to guard against self oscillation.
Figure 8:
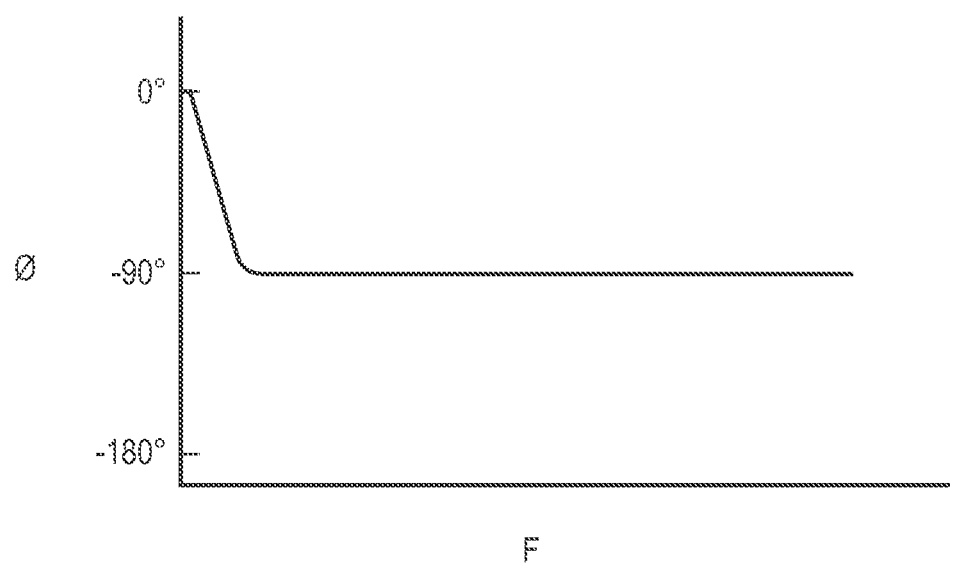
FIG. 8 is a plot of phase shift versus frequency for the amplifier whose gain-frequency response is shown in FIG. 7.

As mentioned before, the control circuit can be regarded as operating much like a operational amplifier. Electronic engineers are generally aware that an amplifier connected in a feedback loop has the capability of entering self sustaining oscillation. Furthermore, most engineers are aware that manufacturers of operational amplifiers guard against self oscillation by deliberately inserting a low frequency pole, i.e. a low pass filter in the amplifier, so as to modify the gain versus frequency response of the amplifier. In broad terms, and as illustrated in FIG. 7, the insertion of a single pole 110 in the frequency response characteristic causes the gain (expressed in decibels) to decrease by −20 dB per decade. This introduces a phase shift as function of frequency of −90° at frequencies above the position of the pole 110, as illustrated at FIG. 8. Most electrical engineers leave University with a working "rule of thumb" that an amplifier or a feedback loop will remain stable as long as the gain of the loop only decreases at −20 dB per decade as the gain in the loop crosses unity.

A consequence of this is that stability can be ensured as long as only one pole exists below the unity gain frequency of the operational amplifier. However, in general it is difficult to ensure that only one pole exists.

Figure 9:
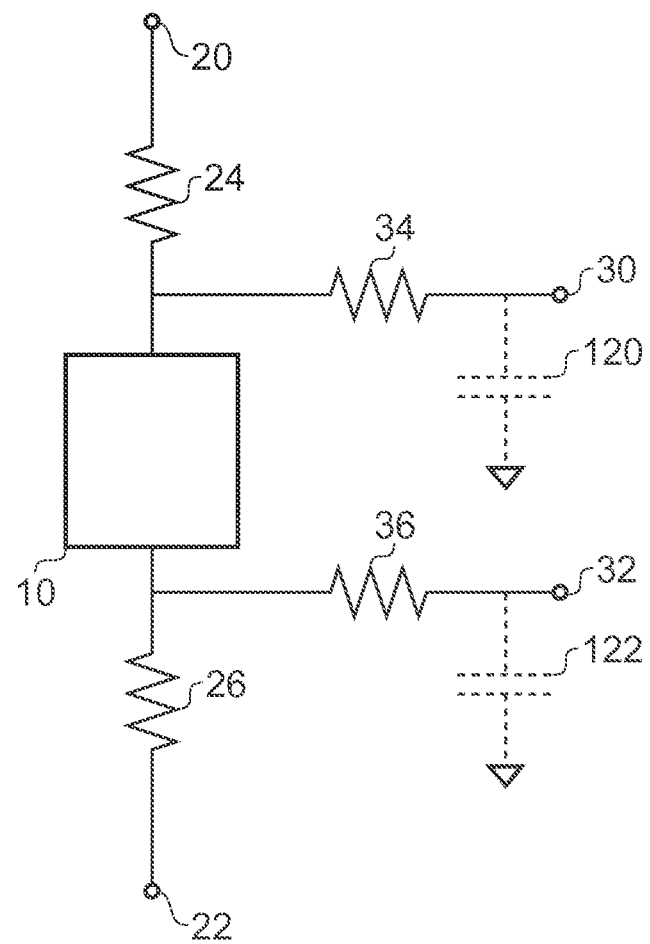
FIG. 9 shows part of the circuit of FIG. 1, but with the inclusion of parasitic components.

FIG. 9 illustrates the four terminal sensor of FIG. 1 in greater detail, but this time includes the effect of parasitic components, and in particular parasitic capacitors 120 and 122. It can be seen that the parasitic capacitance 120 acts in conjunction with the resistor 34 to form a low pass filter whose break point will be determined by the resistance of resistor 34 and the capacitance of the parasitic capacitor 120. This low pass filter places a further pole in the frequency response of the forward signal path within the control circuit. Similarly resistor 36 and parasitic capacitor 122 also form a low pass filter. For simplicity it will be assumed that these two poles are at the same frequency hence can be regarded as being a single low pass filter. If it is not the case that the poles can be regarded as forming a single low pass filter, the generally one will be more troublesome than the other, and measures described herein to restore loop stability will be applied to the more troublesome one of the poles as a matter of preference.

Figure 10:
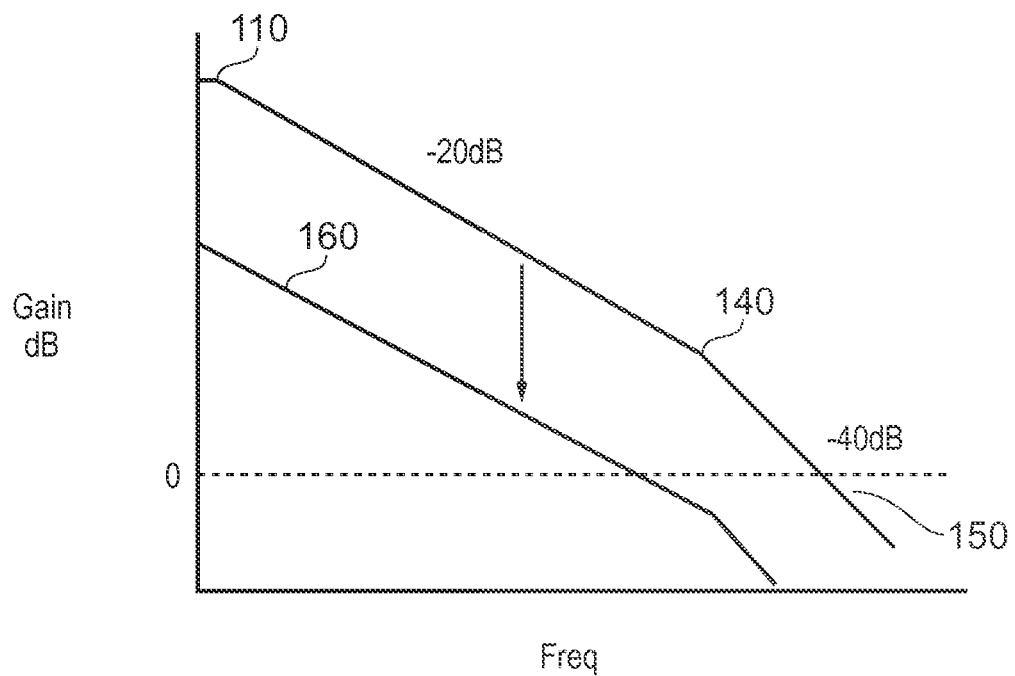
FIG. 10 is a plot of a gain-frequency characteristic for the circuit of FIG. 1 in the absence of any compensating zero in its response characteristic.
Figure 11:
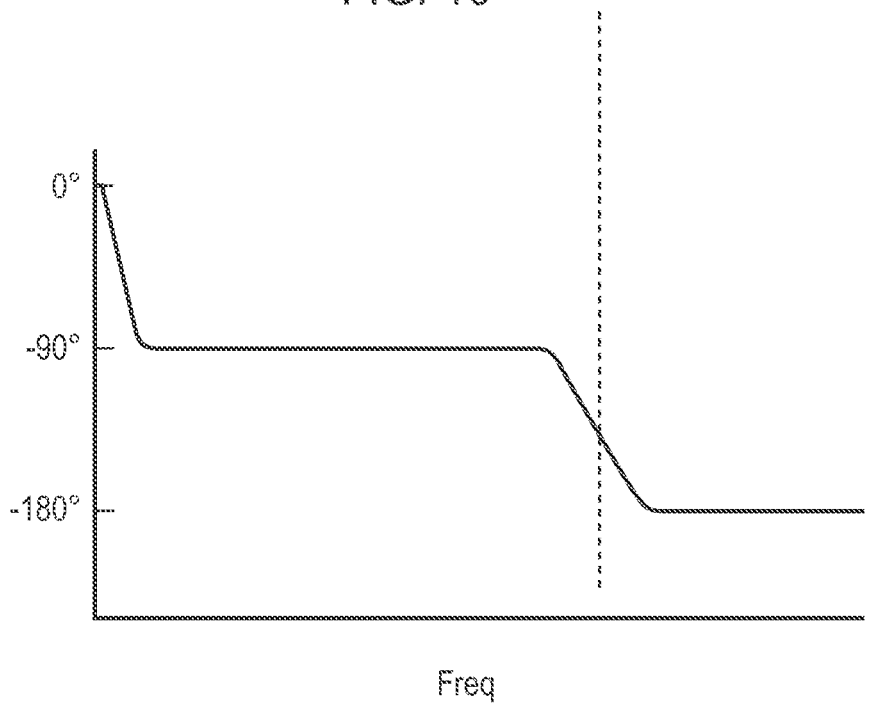
FIG. 11 is a plot of the phase-frequency response for the circuit having the gain-frequency response shown in FIG. 10.

FIG. 10 schematically illustrates frequency response characteristic for the circuit shown in FIG. 1 where a primary pole 110 exists in the control circuit frequency response by virtue of it being included by design in order to provide loop stability, and a further pole 140 exists as a result of the filter inadvertently formed between resistor 34 and parasitic capacitor 120 and resistor 36 and parasitic capacitor 122. If the parasitic pole 140 occurs at a frequency where the open loop gain of the control circuit 6 has not fallen below 0 dB (below unity) then the frequency response has the capability of falling at −40 dB per decade over a region, generally designated 150, where unity gain is reached. Similarly, a second pole will add a further 90° of phase shift in the frequency response, as shown in FIG. 11, such that at the unity gain frequency the phase shift within the control circuit is substantially 180°. This combines with a 180° phase shift by virtue of the negative feedback loop giving a total phase shift of around 360° and consequently placing the circuit in a position where it can undergo self sustaining oscillation. Typically an engineer when faced with this problem knows that the instability can be solved by reducing the open loop gain of the amplifier to a lower value, as indicated by curve 160 of FIG. 10 such that the intercept with the 0 dB line occurs at −20 dB per decade. However whilst this technique brings stability it reduces the open loop gain and consequently increases the error voltage between the reference voltage and the measured voltage difference. Furthermore, the gain necessarily reduces with frequency so the gain at 2 kHz will be 6 dB less than that at 1 kHz, the gain at 10 kHz will, by definition, be 20 dB less than that at 1 kHz and the gain at 20 kHz will be 26 dB less than that at 1 kHz. The errors between the target voltage difference and the reference voltage difference will be correspondingly increased. Thus, it can be seen that this approach to introducing circuit stability carries a significant penalty in measurement accuracy.

Figure 12:
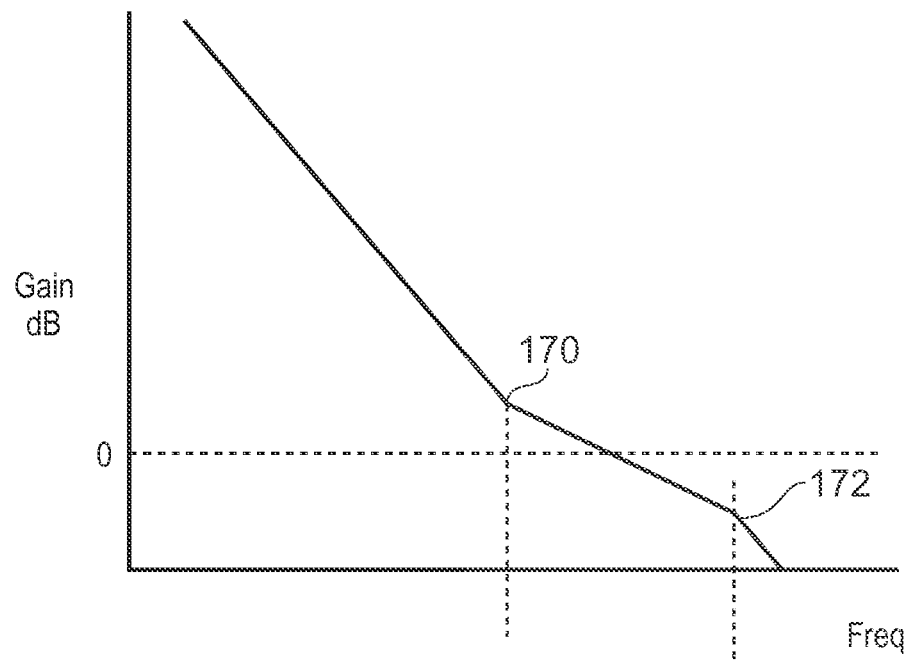
FIG. 12 is a plot of a gain-frequency response for an embodiment of the invention.
Figure 13:
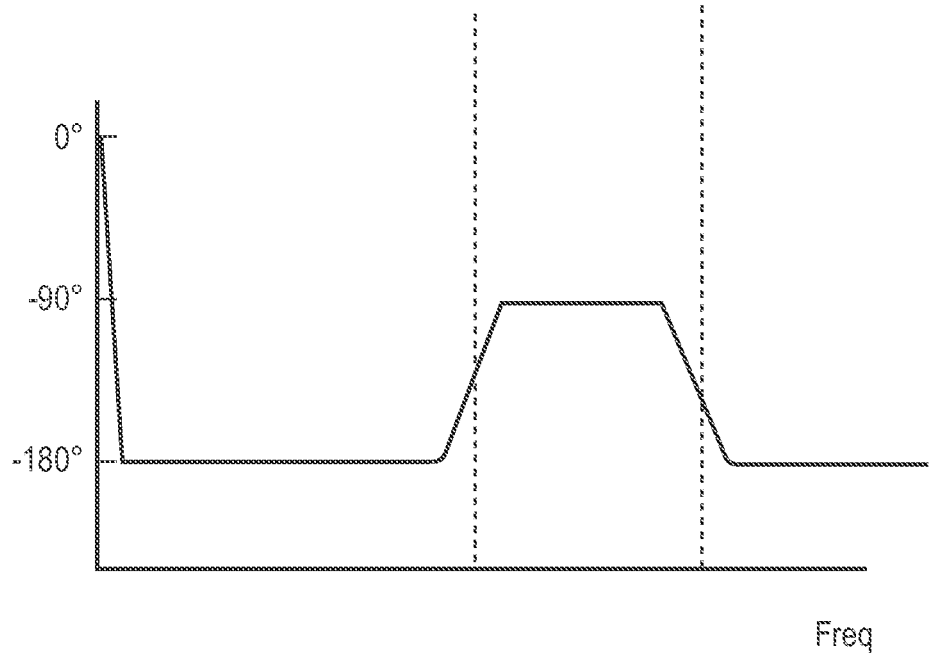
FIG. 13 is a phase-frequency plot for the embodiment whose gain-frequency response is shown in FIG. 12.

Stability against self sustaining oscillation may be resolved by, for example, introducing a zero 170 in the frequency response below the unity gain frequency such that the slope of the frequency response is modified from being −40 dB per decade at frequencies below the zero 170 to −20 dB per decade at frequencies above the zero 170 and at the unity gain frequency. Such an arrangement is shown in FIG. 12. FIG. 12 also shows a further pole 172 occurring at a frequency above the unity gain (zero dB) frequency merely to point out that a pole here does not introduce self sustaining oscillation. FIG. 13 shows a generalized phase plot for such a transfer function which shows the phase change being substantially −180° below the zero 170, rising to substantially −90° between the position of the zero 170 and the pole 172 and reverting back to −180° at frequencies above that of the pole 172.

It is worthwhile pointing out that having a gain change of −40 dB per decade, as shown as occurring at frequencies below that of the zero 170 does not cause oscillation. This is counterintuitive to many electronic engineers. However whether or not a circuit oscillates is determined by the Barkhausen stability criteria. Barkhausen's criteria applies to linear circuits within a feedback loop. It states that if A is the gain of an amplifying element in the forward path of the circuit and β (Jω) is the transfer function of the feedback path so that βA is the loop gain around the feedback loop of the circuit, then the circuit will sustain steady state oscillation only at frequencies for which:

i) the loop gain is equal to unity in absolute magnitude, that is |βA|=1; and ii) the phase shift around the loop is zero or an integer multiple of 2π.

The Barkhausen criteria is a necessary condition for oscillation but it is not a sufficient condition. Some circuits which satisfy the criteria do not oscillate. However if a circuit does not satisfy the criteria then it will not oscillate. This confirms that high gain at relatively low frequencies, as shown in FIG. 12 even though it is accompanied by a phase shift of −180° in the forward path plus a further −180° by virtue of forming the feedback loop (thus corresponding to substantially 2π) will not in itself create an oscillatory condition.

The gain-frequency characteristic of FIG. 12 may be modified by the introduction of further poles and zeros, it being merely sufficient that the frequency response as it crosses the unity gain value falls by only 20 dB per decade. Thus the response towards the lower frequency end of the graph may fall by −40, −60, −80 or more dB per decade depending on how many poles have been introduced in the frequency response characteristic.

Figure 14:
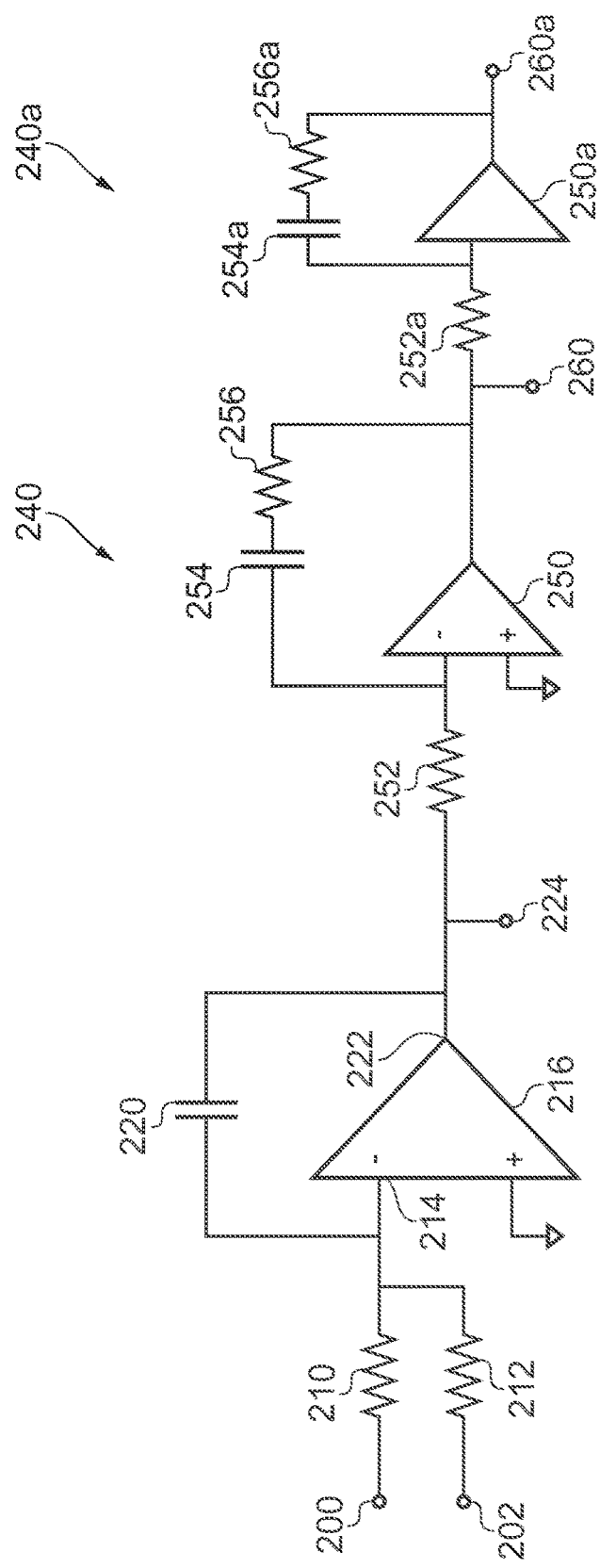
FIG. 14 is a circuit diagram of a circuit in which the first two stages may be used to introduce two poles and one zero, or all three stages may be used to introduce three poles and two zeros.

FIG. 14 illustrates a circuit which provides three poles and two zeros in the frequency response, with a circuit for illustrative purposes only being drawn as a single ended circuit which receives a first input 200 representative of the negated magnitude of the cell output signals and a second input 202 representative of the magnitude of the reference signals. Each of these signals are input via respective impedances 210 and 212 to a inverting input 214 of a first operational amplifier 216. The operational amplifier 216 has its non-inverting input connected to a small signal ground and a capacitor 220 connected between an output 222 of the first amplifier 216 and its inverting input 214. The existence of a capacitor 220 in the feedback loop of the amplifier 216 will be recognized by the person skilled in the art as forming an integrator. An ideal integrator places a pole at 0 Hz. However, given that in reality the amplifier 216 has a finite gain, then the pole is, in reality, positioned close to but not actually at 0 Hz. An output node 224 may be provided so as to selectably allow operation of the circuit as described in the prior art.

However, in accordance with an embodiment of the present invention one or more poles are further provided in conjunction with associated zeros. A pole and zero pair can be provided by a circuit block, generally indicated 240, of which, in this example, two such blocks 240, 240*a* have been provided in series. However the invention can be practiced with the inclusion of only one circuit block 240, or indeed three or more of such circuit blocks. The circuit block 240 includes a further operational amplifier 250 having its non-inverting input connected to a small signal ground. An input resistor 252 is provided between the inverting input of the further operational amplifier 250 and the circuit which supplies a signal to it, which in this instance is the integrator formed around amplifier 216. A feedback loop around the further amplifier 250 comprises a capacitor 254 in series with a resistor 256. It can be seen, that at low frequencies the impedance of the capacitor 254 dominates and hence the feedback loop behaves as an integrator. In this particular arrangement the further pole provided by the circuit block 240 occurs substantially at 0 Hz. It can also be seen that as the frequency rises the impedance of the capacitor 254 reduces and starts to become less significant than that of the further resistor 256. In fact, the value of the capacitance $C_{254}$ of the capacitor 254 and the resistance $R_{256}$ of the resistor 256 inserts a zero at $$\frac{1}{2\pi \cdot R_{256} \cdot C_{254}}.$$

It can further be observed, by inspection, that at frequencies above the frequency of the zero introduced in block 240, the gain of block 240 is determined by the ratio of resistor 256 to the ratio of resistor 252. An output node 260 is provided, such that a signal picked off from this node 260 corresponds to the output node 50 of FIG. 1. Provided that the zero formed by capacitor 254 and resistor 256 occurs below the unity gain frequency of the control circuit 6, then stability will be ensured.

A further block 240a similar to the first block 240, but with similar parts 250a, 252a, 254a 256a, 260a designated by an appended "a" may also be provided to introduce a second pole zero pair. The zero introduced by the further circuit block 240a need not be positioned at the same frequency as the zero provided by the first block 240.

Figure 15:
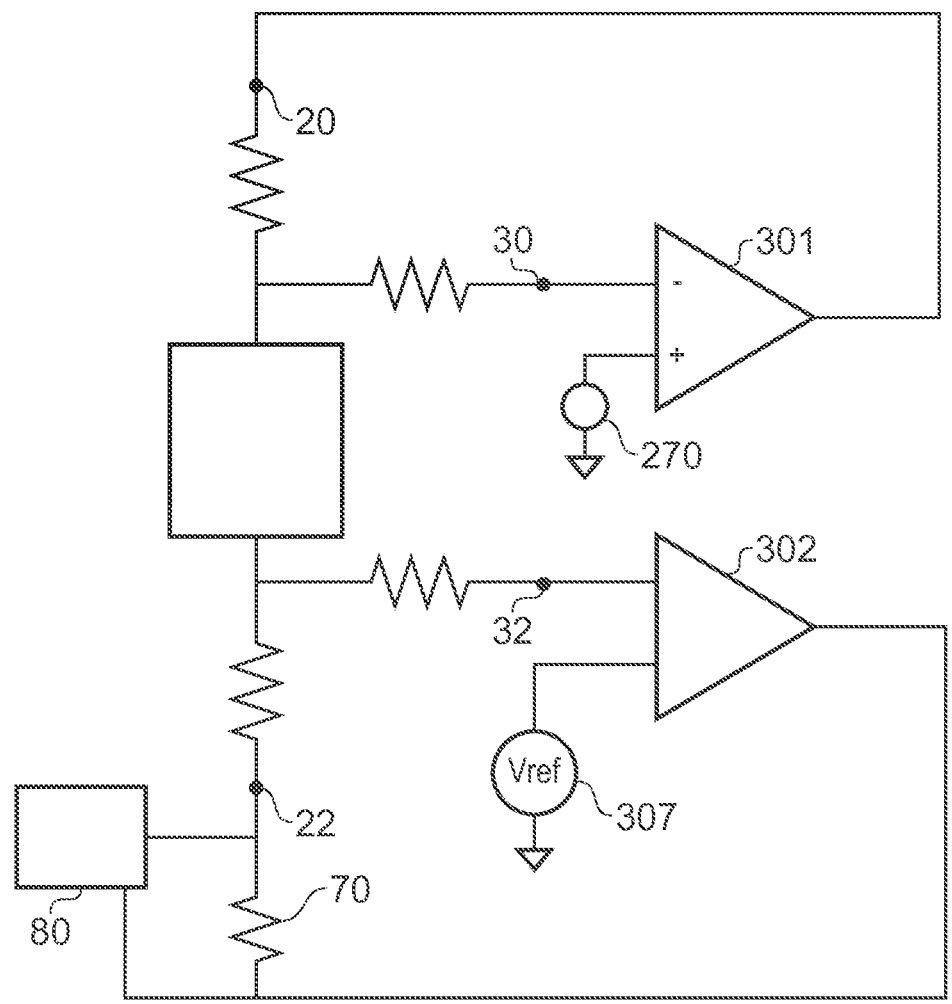
FIG. 15 is a diagram of a differential instrument loop that can be stabilized in accordance with the invention.

FIG. 15 illustrates a further variation of the circuit shown in FIG. 1 where two control circuits are provided. An upper control circuit 301, including additional pole-zero compensation as described hereinbefore receives a first reference voltage from a first reference voltage generator 270 and controls the voltage at the first measurement terminal 30 to match that reference voltage provided by the first reference voltage generator 270. A second control circuit 302 receives a second reference voltage from a second reference voltage generator 307 and controls the voltage at the second measurement terminal 32 to be equal to the voltage from the second reference voltage generator 307. Thus upper and lower limbs of the sensor are driven to respective voltages in a dual ended manner. A current measuring resistor 70 may be inserted in either of the control loops (as by definition the current must be the same in each control loop, and the voltage occurring across the resistor 70 can be digitized by a differential input analog to digital converter 80.

Figure 16:
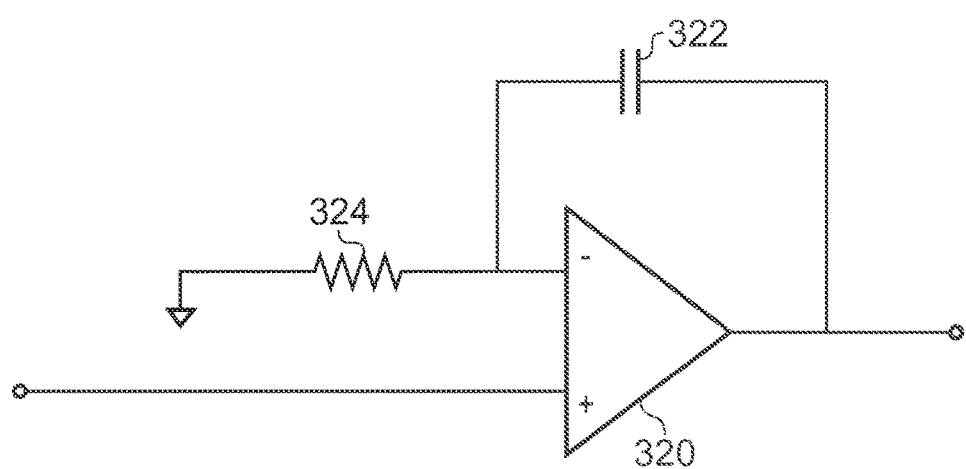
FIG. 16 is a circuit diagram of a further circuit for introducing a pole zero pair.

FIG. 16 is a circuit diagram of a further circuit that can be used to provide a pole zero pair as is known to the person skilled in the art. It comprises an operational amplifier 320 having a non inverting input that acts as a signal input. A capacitor 322 is connected between an output of the amplifier 320 and an inverting input of the amplifier 320. A resistor 324 connects the inverting input to a small signal ground.

It should be noted that the designer may also place zeros in the transfer characteristic without forming an associated pole. Such a zero can be implemented as a high pass filter, either as an active filter of a passive filter, as is known to the person skilled in the art.

It is thus possible to modify the frequency response of the or each control circuit by the appropriate insertion of additional poles (preferably as integrators) and zeros (preferably as high pass filters) so as to enable much higher loop gains to be employed than would be the case if stability was ensured by merely reducing the open loop gain of the control circuit by use of gain reduction alone rather than by introduction of additional pole zero pairs.

The claims presented here are written in single dependent format so as to be suitable for filing at the USPTO. However, for use in other jurisdictions where multiple dependent claims are frequently used, each dependent claim is to be assumed to be multiply dependent on all preceding dependent claims sharing the same independent claim, except where this is clearly not technically feasible.

The invention claimed is:

1. A control circuit configured to couple to a biological sensor, the control circuit comprising:
an excitation output node configured to provide current for a variable impedance of the biological sensor;
a sensor input configured to receive a signal indicative of a voltage across the variable impedance;
a multiple-stage amplifier configured to receive the signal and to adjust an excitation voltage at the excitation output node based on a comparison of the signal and a reference voltage,
wherein a feedback path of a first stage of the multiple-stage amplifier is configured to provide a zero of a transfer characteristic of the control circuit at a frequency where the gain of the control circuit is greater than unity gain.

2. The control circuit of claim 1, wherein the transfer characteristic of the control circuit includes N poles and N−1 zeros; and
wherein N is an integer greater than 2.

3. The control circuit of claim 2, wherein one of the N poles is implemented using an integrator.

4. The control circuit of claim 2, wherein a pole and zero pair of the N poles and the N−1 zeros is provided by a series combination of a capacitor and a resistor in a feedback loop of an operational amplifier of the first stage.

5. The control circuit of claim 1, comprising a signal generator for generating the reference signal at a plurality of frequencies.

6. The control circuit of claim 1, comprising a current sensor for measuring current of the biological sensor.

7. The control circuit of claim 6, further comprising a phase detector for detecting a phase difference between the voltage and the current.

8. The control circuit of claim 1, wherein the multiple-stage amplifier includes a second stage having a second amplifier configured to contribute an additional pole and an additional zero to the transfer characteristic of the control circuit.

9. The control circuit of claim 1, wherein an integrated circuit includes the multiple-stage amplifier and the feedback path.

10. The system of claim 1, wherein the excitation output is a differential excitation output.

11. The system of claim 1, wherein the excitation output is a single-ended excitation output.

12. A system comprising:
a sensor having a variable impedance; and
a control circuit, the control circuit configured to provide an excitation signal to the variable impedance and to receive a signal indicative of a voltage across the variable impedance;
wherein the control circuit includes:
an multiple-stage amplifier configured to receive the signal and to adjust the excitation current based on a comparison of the signal and a reference voltage; and
a feedback path of a first stage of the multiple-stage amplifier, the feedback path coupled between an input of the first stage and an output of the first stage, and the feedback path configured to provide a zero of a transfer characteristic of the control circuit at a frequency where the gain of the control circuit is greater than unity gain.

13. The system of claim 12, wherein the sensor includes a four terminal sensor having an impedance that changes in response to a measurand.

14. The system of claim 13, wherein the measurand is a biological sample.

15. The system of claim 12, wherein the sensor is configured to receive a blood sample; and
wherein the control circuit is configured to provide an indication of a blood glucose level of the blood sample.

16. The system of claim 12, wherein, during a biological parameter test of a biological sample, the control circuit is configured to hold a substantially constant DC voltage across the variable impedance of the sensor.

17. The system of claim 12, wherein the excitation signal is a differential excitation signal.

18. The system of claim 12, wherein the excitation signal is a single-ended excitation signal.

19. A control circuit configured to couple to a biological sensor, the control circuit comprising:
- an excitation output node configured to provide current for a variable impedance of the biological sensor;
- a sensor input configured to receive a signal indicative of a voltage across the variable impedance;
- a multiple-stage amplifier configured to receive the signal and to adjust an excitation voltage at the excitation output node based the signal; and
- wherein a first stage of the multiple-stage amplifier includes means for changing phase of a transfer function of the control circuit.

20. The control circuit of claim 19, wherein the means for changing phase is a high pass filter.

21. The control circuit of claim 19, wherein the means for changing phase is an active filter.

22. The control circuit of claim 21, wherein the active filter includes:
- an amplifier;
- a capacitor;
- a resistor; and
- wherein the capacitor and resistor are coupled in series between an input of the amplifier and an output of the amplifier.

23. The control circuit of claim 19, wherein the means for changing phase is configured to provide a slope of a loop gain of the control circuit of −20 dB or more per decade change of frequency at a unity gain frequency of the control circuit.

24. The control circuit of claim 23, wherein the means for changing phase is configured to provide a zero of a transfer characteristic of the control circuit at the frequency where the loop gain of the control circuit is greater than unity gain.

* * * * *